US012370126B2

(12) United States Patent
Mojarrad et al.

(10) Patent No.: US 12,370,126 B2
(45) Date of Patent: Jul. 29, 2025

(54) SYSTEMS AND APPROACHES FOR DRUG DELIVERY DEVICE RECONSTITUTION

(71) Applicant: AMGEN INC., Thousand Oaks, CA (US)

(72) Inventors: Mehran Mojarrad, Thousand Oaks, CA (US); Scott R. Gibson, Granada Hills, CA (US); Xiaotong Li, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 223 days.

(21) Appl. No.: 17/763,681

(22) PCT Filed: Oct. 16, 2020

(86) PCT No.: PCT/US2020/055872
§ 371 (c)(1),
(2) Date: Mar. 25, 2022

(87) PCT Pub. No.: WO2021/076824
PCT Pub. Date: Apr. 22, 2021

(65) Prior Publication Data
US 2022/0331204 A1 Oct. 20, 2022

Related U.S. Application Data

(60) Provisional application No. 62/923,040, filed on Oct. 18, 2019.

(51) Int. Cl.
*A61J 1/20* (2006.01)
*A61M 39/16* (2006.01)
*A61M 39/22* (2006.01)

(52) U.S. Cl.
CPC ............ *A61J 1/2089* (2013.01); *A61M 39/16* (2013.01); *A61M 39/223* (2013.01); *A61M 2209/06* (2013.01)

(58) Field of Classification Search
CPC ...... A61J 1/2079; A61J 1/2006; A61J 1/2093; A61J 3/002; B65D 81/32; B65B 3/003;
(Continued)

(56) References Cited

U.S. PATENT DOCUMENTS

| 4,915,688 A * | 4/1990 | Bischof .................. A61M 39/02 604/83 |
| 6,615,880 B2 * | 9/2003 | Hewlitt .................... B67D 7/74 141/105 |

(Continued)

FOREIGN PATENT DOCUMENTS

| WO | WO-2010043685 A1 | 4/2010 |
| WO | WO-2010141632 A2 | 12/2010 |

OTHER PUBLICATIONS

Julia Stieglmaier , Jonathan Benjamin & Dirk Nagorsen (2015) Utilizing the BiTE (bispecific T-cell engager) platform for immunotherapy of cancer, Expert Opinion on Biological Therapy, 15:8, 1093-1099, DOI: 10.1517/14712598.2015.1041373 (Year: 2015).*

(Continued)

Primary Examiner — Nicholas J. Weiss
Assistant Examiner — Gabriella E Burnette
(74) Attorney, Agent, or Firm — MARSHALL, GERSTEIN & BORUN LLP

(57) ABSTRACT

Drug reconstitution systems and related methods are disclosed herein. A drug reconstitution system may include a first component in a first container in a storage state and a second component in a second container in a storage state. The first component may be selected from a group of a drug product, a diluent, a saline solution, and an IV stabilizing solution ("IVSS"). The second component may be selected from a group of the drug product, the diluent, the saline solution, and the IVSS. The first component may be different than the second component. At least one fluid path may be (Continued)

configured to at least selectively fluidly connect the first container and the second container. An urging assembly may be configured to selectively urge at least a portion of the first component from the first container and into contact with the second component.

16 Claims, 3 Drawing Sheets

(58) Field of Classification Search
CPC . A61M 39/16; A61M 39/223; A61M 2209/06
See application file for complete search history.

(56) References Cited

U.S. PATENT DOCUMENTS

| | | | |
|---|---|---|---|
| 2009/0198217 A1* | 8/2009 | Thorne, Jr. | A61M 5/162 604/83 |
| 2014/0114275 A1* | 4/2014 | Creaturo | A61J 1/201 141/2 |
| 2015/0257974 A1 | 9/2015 | Demers et al. | |
| 2017/0232187 A1 | 8/2017 | McNall, III et al. | |

OTHER PUBLICATIONS

Blinatumomab prescribing information (Year: 2014).*
Goyos, A, et al. ,"Generation of Half-Life Extended Anti-BCMA Bite® Antibody Construct Compatible with Once-Weekly Dosing for Treatment of Multiple Myeloma (MM)" vol. 130, Supplement 1, 2017, p. 5389, ISSN 0006-4971, https://doi.org/10.1182/blood.V130. Suppl_1.5389.5389. (Year: 2017).*
FDA report NDC 0310-4715 IV Solution Stabilizer (Year: 2024).*
International Search Report issued to International Application No. PCT/US2020/055872, dated Feb. 1, 2021.
Written Opinion of the International Searching Authority issued to International Application No. PCT/US2020/055872, dated Feb. 1, 2021.
Australian Patent Application No. 2020366423, Examination Report, dated Apr. 4, 2025.

* cited by examiner

SYSTEMS AND APPROACHES FOR DRUG DELIVERY DEVICE RECONSTITUTION

CROSS-REFERENCE TO RELATED APPLICATIONS

This is the United States national phase of International Patent Application No. PCT/US20/55872, filed Oct. 16, 2020, which claims the priority benefit of U.S. Provisional Application No. 62/923,040, filed Oct. 18, 2019, entitled "Systems And Approaches For Drug Delivery Device Reconstitution," the entire contents of each of which are hereby incorporated by reference herein.

FIELD OF DISCLOSURE

The present disclosure generally relates to drug delivery devices and, more particularly, to reconstitution approaches for drug delivery devices.

BACKGROUND

Drugs are administered to treat a variety of conditions and diseases. Intravenous ("IV") therapy is a drug dosing process that delivers drugs directly into a patient's vein using an infusion contained in a delivery container (e.g., a pliable bag). These drug dosings may be performed in a healthcare facility, or in some instances, at remote locations such as a patient's home. In certain applications, a drug product may be shipped to a healthcare facility (e.g., an inpatient facility, an outpatient facility, and/or a pharmacy) in a powdered or lyophilized form.

When reconstituting these drugs for administration, it is of particular importance to maintain a sterile environment so as to not taint or otherwise damage the quality of the drug. Additionally, some classes of drugs such as bi-specific T-cell engagers may require exceptionally accurate quantities of the drug product and/or other fluids required for dosing so as to prevent the drug product from becoming toxic. Oftentimes, the healthcare professional must prepare the drug by closely following a set of steps to ensure a sterile environment is maintained and that correct quantities of ingredients are added to the delivery container. When reconstituting these drugs for administration, it may be desirable or necessary to utilize a diluent, such as by adding a diluent to a drug product vial. As a result of these various steps and requirements, the reconstitution process may be time-consuming, tedious, and may have an unacceptable or undesirable error rate.

The current process of reconstituting a lyophilized oncology product is often done either at the hospital or the specialty compounding pharmacy by a licensed pharmacist. The use of a hood is often required to perform reconstitution steps to provide a sterile working environmental which can be cumbersome for pharmacist given the complexity of the steps. In addition, this reconstitution process involves the use of multiple needles to withdraw/add sterile water for injection (WFI), saline and/or Intravenous Solution Stabilizer (IVSS) solutions. Typically, for relatively complex oncology products such as a Bi-specific T-cell Engager (BiTE®) molecule (e.g. Blincyto®) prepared in an IV bag, a specified volume of WFI is added to reconstitute a lyophilized drug product contained in a vial via the use of a needle and syringe system. Then, the applicable volume of saline and IVSS solutions are added to an empty IV bag before the final reconstituted drug product is introduced. The overall process may take up to 5 needle and syringe systems, each of which carries manual labor time and exposure to a potential needle. Furthermore, the use of a hood during this complex preparation may introduce risks.

In addition, with the current regulatory requirements implemented by National Institute for Occupational Safety and Health (NIOSH), certain oncology products are included in the hazardous drug list which require the use of additional engineering controls such as Closed System Transfer Device (CSTD) as an additional means of protection. Also, regardless of whether a drug is on the NIOSH list, it may be advantageous to utilize a CSTD and/or other components/systems to minimize or avoid undesired release of fumes into the air or other exposures.

As described in more detail below, the present disclosure sets forth systems and methods for drug delivery device reconstitution embodying advantageous alternatives to existing systems and methods, and that may address one or more of the challenges or needs mentioned herein, as well as provide other benefits and advantages.

SUMMARY

An aspect of the present disclosure provides a drug reconstitution system including a first component, a second component, at least one fluid path, and an urging assembly. The first component may be selected from a group of a drug product, a diluent, a saline solution, and an IV stabilizing solution ("IVSS"). The first component may be in a first container in a storage state. The second component may be selected from a group of the drug product, the diluent, the saline solution, and the IVSS. The first component may be different than the second component and the second component may be in a second container in a storage state. The at least one fluid path may be configured to at least selectively fluidly connect the first container and the second container. The urging assembly may be configured to selectively urge at least a portion of the first component from the first container and into contact with the second component.

An additional aspect of the present disclosure provides a method of preparing a drug for delivery. The method may include: (a) providing a diluent contained in a diluent container; (b) providing a drug product container within a drug product container; (c) providing a fluid path system physically connecting the diluent container and the drug product container, the fluid path system having a storage configuration wherein the diluent container and the drug product container are not in fluid communication with each other and a first mixing configuration wherein the diluent container and the drug product container are in fluid communication with each other; and (d) adjusting the fluid path system from the storage configuration to the first mixing configuration to urge at least a portion of the diluent from the diluent container and/or at least a portion of the drug product from the drug product container to form a drug product/diluent mixture.

BRIEF DESCRIPTION OF THE DRAWINGS

The above needs are at least partially met through provision of the systems and approaches for drug delivery device reconstitution described in the following detailed description, particularly when studied in conjunction with the drawings, wherein.

Figure 1:
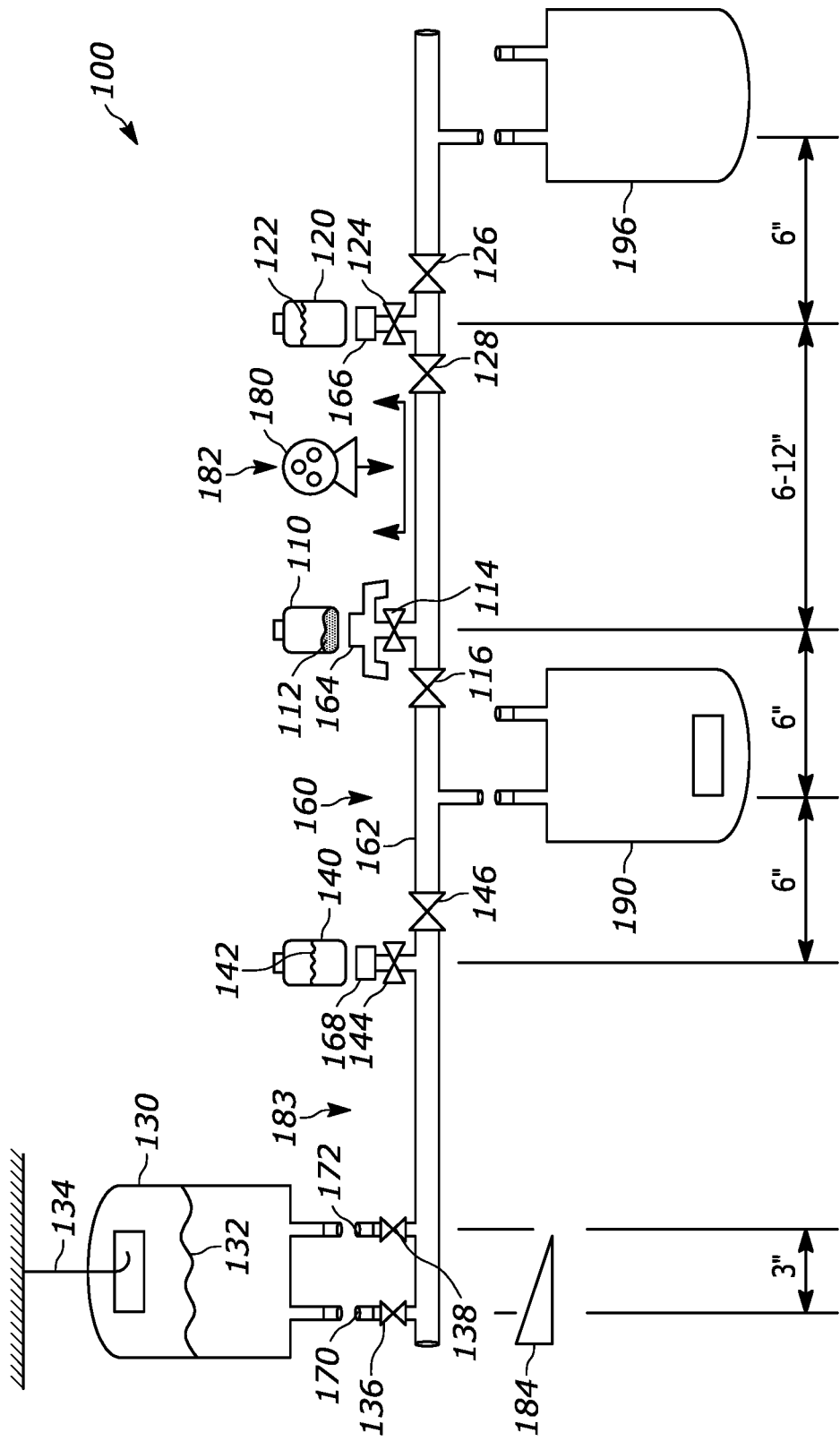
FIG. 1 illustrates exemplary drug reconstitution system in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure relates to a closed drug preparation system that provides the sterile environment that could enable an improved preparation environment, thereby reducing risk and the number of steps for preparation. As a more specific example, the present disclosure relates to a system and method that may offer benefits and/or precautions of a Closed System Transfer Device (CSTD), but while providing a disposable, portable, and user-friendly system or method.

As a more specific example, drug reconstitution systems and methods are described herein, which may generally include: a first component selected from a group of a drug product, a diluent, a saline solution, and an IV stabilizing solution ("IVSS"), wherein the first component is in a first container in a storage state; a second component selected from a group of the drug product, the diluent, the saline solution, and the IVSS, wherein the first component is different than the second component and the second component is in a second container in a storage state; at least one fluid path configured to at least selectively fluidly connect the first container and the second container; and an urging assembly configured to selectively urge at least a portion of the first component from the first container and into contact with the second component.

The urging assembly may include one or more of the following: a pump at least selectively coupled with the at least one fluid path, at least one fluid path valve, at least one fluid path clamp, at least one fluid path closing component, at least one gravitational flow differential, a ramped surface, a raised container support, or one or more load cells.

The drug reconstitution system may include a third component selected from a group of the drug product, the diluent, the saline solution, and the IVSS, wherein the third component is different than the first component and the second component. The third component is in a third container in a storage state. The first, second, and third containers may be packaged as common kit packaging.

The drug reconstitution system may include a fourth component selected from a group of the drug product, the diluent, the saline solution, and the IVSS, wherein the fourth component is different than the first component, the second component, and the third component. The fourth component is in a fourth container in a storage state. The first, second, third, and fourth containers may be packaged as common kit packaging.

The drug reconstitution method may include, generally: providing a fluid path system physically connecting a diluent container and a drug product container, the fluid path system having a storage configuration wherein the diluent container and the drug product container are not in fluid communication with each other and a first mixing configuration wherein the diluent container and the drug product container are in fluid communication with each other; and adjusting the fluid path system from the storage configuration to the first mixing configuration to urge at least a portion of the diluent from the diluent container and/or at least a portion of the drug product from the drug product container to form a drug product/diluent mixture.

The drug reconstitution method may also include adjusting the fluid path system to a second mixing configuration to urge at least a portion of a saline solution from a saline container and/or at least a portion of an IVSS from an IVSS container to form a saline/IVSS mixture.

As another example, a sterile disposable tubing manifold and other components may be utilized to reconstitute a lyophilized drug product for point of care use. As a more specific example, a disposable tubing manifold and other components facilitate all the necessary steps to perform a reconstitution process to provide a "closed" process for the user to potentially eliminate the requirement of a hood and any safety risks associated with the use of multiple needles to reconstitute drug products such as oncology medications. Additionally, the system can have integrated automation capabilities to allow the patients to perform reconstitution themselves in preparation for self-administration of the drug with their delivery device.

The system may include a sterile single-use tubing system and valve system is used to reconstitute the lyophilized compound to the final IV bag the patient will be receiving. This system can be modular in nature where different size/Volume solutions are integrated. In one application, the tubing manifold is manual and is used by a pharmacist or a health care provider suitably trained in preparing similar drug doses. In another application, the system is even more user-friendly and/or automated to enable the patients to perform the reconstitution themselves.

Turning to FIG. 1, pursuant to these various embodiments, a drug delivery system 100 or kit and a corresponding method of preparing a drug delivery device using the drug delivery system 100 are provided. The drug delivery system 100 can be used by a healthcare professional, a caregiver, or patient to prepare a drug delivery device to be delivered to a patient. The drug delivery system 100 varies from conventional systems in that a number of the components included in the system 100 come prefilled and/or premixed in correct dosage quantities. As a result, preparation of the drug delivery device by the healthcare professional, caregiver, or patient is reduced while still ensuring correct quantities of ingredients are administered. The system 100 may be used to provide intravenous, subcutaneous, intra-arterial, intramuscular, and/or epidural delivery approaches. By using the system 100, patient anxiety and or confusion may be reduced due to reduced preparation complexity and wait times caused by the drug preparation process. Additionally, the system 100 may permit a health care provider, a pharmacist, a patient, and/or other individuals involved in preparing, providing, or using medication to have a more streamlined, predictable, and/or effective process for drug delivery. For example, the system 100 may reduce the amount of time a pharmacist spends preparing medication for use by a patient, reduce the number of steps a pharmacist must manually take to prepare medication for use by a patient, and/or improve the overall efficiency of the medication preparation process. As a more specific example, the system 100 may be particularly advantageous for use with medication preparation that involves several steps, such as adding a diluent and then adding a solution containing saline and/or IVSS, and/or medication that requires extensive preparation time.

The drug delivery system 100 shown in FIG. 1 includes, generally, a drug product container 110 containing a drug product 112; a diluent container 120 containing a diluent 122; a saline container 130 containing a saline solution 132; an IV stabilizing solution ("IVSS") container 140 containing an IVSS 142; and a fluid path assembly 160 configured to selectively, fluidly couple or de-couple various of the aforementioned components.

For example, the fluid path assembly 160 may include a tubing manifold 162 having a series of connection points for physically connecting the respective containers 110, 120, 130, and 140 with each other. As a more specific example, the connection points may include quick-connect sterile connectors with respective sub-components that selectively mate with each other while maintaining sterility or another desirable cleanliness standard. For example, the quick-connect sterile connectors may snap or twist or screw together; they may have sheathed or covered components that become unsheathed or uncovered upon connection; and/or they may have Luer Lock or modified Luer Lock configurations. As another example, the connectors may include one or more stake connectors for coupling one of the tube 162 portions with an IV bag.

Turning to FIG. 1, for example, adaptor 164 may be a closed system transfer device ("CSTD") or a suitable vial adaptor that matingly fits with the drug product container 110, which may be a vial. Similarly, adapter 166 may be a vial adaptor that matingly fits with the diluent container 120, which may also be a vial. Similarly, adapter 168 may be a vial adaptor that matingly fits with the IVSS container 140, which may be a vial. Any or all of the containers 110, 120, 140 may be a vial with a standard septum that is pierced by a vial adapter or a vial stake; additionally or alternatively any or all of the containers 110, 120, 140 may include a quick-connect sterile connector or other suitable connector. Alternatively, any or all of the containers 110, 120, 140 may be a resilient container such as an IV bag or any other suitable container. Although each of the containers 110, 120, 140 is shown in FIG. 1 in an up-right configuration, it may be connected with the fluid path assembly 160 by turning the container upside-down and permitting the contents to drain via gravity. However, if the drug product 112 or other component is in solid form then it may be beneficial or desirable to urge a fluid into the vial to reconstitute the solid component to facilitate and/or improve the draining process.

The saline container 130 may be an IV bag, a vial, or any other suitable container. The saline container 130 is coupled with the fluid path assembly 160 via one or more ports 170, 172 as shown in FIG. 1. For example, IV spikes (not shown) may pierce the ports 170, 172 to physically connect the saline container 130 to the fluid path assembly 160. The IV bag shown in FIG. 1 is coupled with a hook 134 for hanging the bag and providing gravity draining capabilities.

The system 100 shown in FIG. 1 also includes a final drug product bag 190 for collecting and storing the final mixture of the drug product, which can then be delivered to a patient and/or stored. The system 100 also includes a waste bag 196 that receives extraneous amounts of the components and/or final drug product. Although both of these components are shown in the system 100 in FIG. 1, a system 100 may operate without one or both of these containers, such as by storing the final mixture of drug product in one of the other containers 110, 120, 130, 140 and/or by holding extraneous amounts of the components and/or final drug product in a container and/or the length of the tube 162.

The containers 110, 120, 130, 140 shown in FIG. 1 are each in a storage state where they are not fluidly coupled with each other. Once the containers 110, 120, 130, 140 shown in FIG. 1 are each physically connected to the fluid path assembly 160 as described above or another suitable means, they may still remain in the storage state and not fluidly coupled with each other. For example, even once the containers 110, 120, 130, 140 are each fluidly coupled with different portions of the fluid path assembly 160, the containers may be fluidly de-coupled or separated from each other via one or more fluid closing component such as a valve or a clamp that promotes or causes occlusion. As a more specific example, FIG. 1 shows a series of valves that are able to individually and/or collectively fluidly separate the containers from each other. Valve 124 is positioned adjacent to the adapter 166 so that, even when the diluent container 120 is connected to the adapter 166 and gravitational forces are acting on the diluent 122, the diluent 122 does not flow into fluid contact with any of the other containers 110, 130, 140. As shown in FIG. 1, the valve 124 is positioned along a generally vertical portion of tube 162, but other configurations may be suitable. Valves 126 and 128 are each positioned along a generally horizontal portion of the tube 162 on opposite sides of the vertical portion, such that the valve 126 controls access to portions of the fluid path assembly 160 that lead to the drug product container 110 and the valve 128 controls access to portions of the fluid path assembly 160 that lead to the waste bag 196.

The system 100 shown in FIG. 1 further may include a valve 114 positioned along a vertical portion of the tube 162 adjacent to the drug container 110 that selectively restricts fluid connection with the same. Similarly, the system 100 includes a valve 116 positioned along a horizontal portion of the tube 162 adjacent to the final drug product container 190 and selectively restricting fluid connection with the same from the drug product/diluent side of the system 100.

The system 100 shown in FIG. 1 also may include a pair of valves 136, 138 positioned along the vertical portions of the tube 164 supporting the adapters 170, 172, thereby selectively restricting fluid connection between the saline container 130 and other containers. The system 100 shown in FIG. 1 further may include a valve 144 positioned along a vertical portion of the tube 162 adjacent to the IVSS container 140 that selectively restricts fluid connection with the same. Similarly, the system 100 includes a valve 146 positioned on a horizontal portion of the tube 162 adjacent to the final drug product container 190 and selectively restricting fluid connection with the same from the saline/IVSS side of the system 100.

The fluid closing components utilized in the system may be any suitable components or features that selectively permit or restrict fluid movement within the fluid path assembly 160. For example, if the fluid closing components are valves then they may have external handles that, when turned, open or close a ball joint portion contained therewithin. As a more specific example, the valves may be one-way, two-way, three-way, or other types of stop valves that are suitable for selectively stopping or restricting flow.

As another example, the fluid closing components utilized in the system may be clamps that pinch a localized section of the tube 162 and prohibit or restrict fluid flow therethrough. Such clamps are preferably removable, such as squeeze clamps, that have sufficient clamping force to completely or substantially occlude a desired portion of the tube 162. It may be advantageous to utilize pinch clamps that can be moved from one location to the next to reduce the total number of system components. Additionally, the fluid closing components may be manually operated, such as manual valves or clamps, or they may be automatically controlled, such as electronic valves or flow restrictors, that are controlled by a system controller or a central processing unit ("CPU") (shown in FIG. 2).

Although the above-described fluid closing components may selectively restrict or prohibit flow therethrough, they may also serve as components of an urging assembly, particularly when paired with other component(s). For example, a pump 180, a gravitational flow differential (e.g., the sloped configuration illustrated by ramp 184), or a raised container support (e.g., the hook 134 and/or the vertical portions of the tube supporting the containers 110, 120, 140) may be configured to selectively urge contents of one container towards and/or into fluid contact with the contents of another container.

The pump 180 shown in FIG. 1 is in a first position 182 along the fluid path between the diluent container 120 and the drug product container 110. The pump 180 may also be used in a second position 183, along the fluid path between the saline container 130 and the IVSS container 140. The system 100 may include a single pump movable between two locations, a single pump that is not movable, two or more pumps that are not movable, or another suitable configuration. In the case of a single pump, the system 100 may rely on gravitational flow and/or raised container support to selectively urge contents of one container towards and/or into fluid contact with the contents of another container. The pump 180 shown in FIG. 1 is preferably a portable peristaltic pump, but other types of pumps may be used. Alternatively or additionally, a positive displacement type pump may be used, although such a pump may be more difficult to move from one location to another within the system 100.

One objective of the system 100 shown in FIG. 1 may be to utilize the disposable tubing manifold design (fluid flow path assembly 160 and other containers, adapters, and valves) to incorporate all the necessary components during complex oncology therapy reconstitution process into a single manifold to reduce the safety risks associated with needles as well as hazardous drugs. In this disposable tubing manifold design, the tube 162 may be manufactured, assembled and gamma irradiated to become sterile and ready to use. The tubing manifold, sterile quick connects, vial adapters, and CSTD are integrated to provide the appropriate connections to each compound required during reconstitution. It should be noted that:

- The tubing manifold design is intended to be flexible where additional connections can be added to accommodate other Drug Product (DP) compound additions;
- The tubing manifold is modular in nature, therefore different volumes of diluent, DP, and IVSS can be attached based on the application/use case;
- The final drug product bag can be flexible in volume in case of a weight-based dose regime;
- In the case where a saline or WFI bag is used, it may be hung to gravity grain and eliminate air;
- An optional waste bag can also be added to the tubing manifold to provide for any drainage required;
- Each tubing segment length and placement of bags or vials along the tubing manifold can be modified based on use case and to reduce overall hold up volumes;
- The overall tubing manifold may be used at a slope to provide best drainage as well as filling minimizing air gaps and fill.

During one exemplary method of operating the system 100, the following steps may be utilized:

Step 1: Add diluent 122 to the drug product container 110 by isolating the desired fluid path, namely by:
  (a) closing valves 126 and 116;
  (b) opening valves 124, 128, 114; and
  utilizing the pump 180 in the first position 182 to urge the diluent 122 into the drug product container 110.

Step 2: Isolate the mixture of diluent 122 and drug product 112 in a horizontal portion of the tube 162 by closing valves 124 and 114.

Step 3: Add IVSS 142 to the saline container 130 by isolating the fluid path and outlet of saline bag, namely:
  (a) closing valves 146 and 172;
  (b) opening valves 136 and 144; and
  (c) utilizing the pump 180 in the second position 183 to urge the IVSS into the saline container 130.

Step 4: Transfer the mixture of saline 132 and IVSS 142 to the final drug product bag 190, namely:
  (a) close valve 136 and 144;
  (b) open valve 138 and 146 to allow the IVSS/saline mixture to flow into the final drug product container 190.

For this step, it may be desirable or advantageous to operate the pump 180 in the second position 183 but in an opposite direction from step 3, namely, to pump the mixture towards the final drug product container 190.

Step 5: Close valve 146, open valve 116, and allow the mixture of drug product 112 and diluent 122 to flow into the final drug product container 190. For this step, it may be desirable or advantageous to operate the pump 180 in the first position 182 to pump the mixture towards the final drug product container 190.

Note that the volumes added/attached to the tubing manifolds have been calculated prior to performing the steps. The final form of any of the solution containers may be any of the vial, bag or prefilled syringe configuration.

In some scenarios, withdrawing liquid from any one of the containers 110, 120, 130, and 140 may cause a vacuum effect within the container, which may increase the suction force needed for removing fluid from the container. To counteract this vacuum effect, some or all of the containers 110, 120, 130, and 140 may incorporate at least one vent which permits air or another gas to fill the container as fluid is withdrawn from the container. Additionally, in some embodiments, the system 100 may include one or more mechanisms to prevent gas pulled in through the vent from being drawn into the fluid path after the container with which the vent is associated has been emptied. Such mechanisms may include for example: a timer configured to turn off the pump 180 after a certain amount of operating time; a scale coupled with one or more of the containers 110, 120, 130, and 140 to determine when the container is empty; a hydrophilic filter coupled to an outlet of one or more of the containers 110, 120, 130, and 140 and configured to allow the passage of fluid but not gas; a trip switch coupled to the pump 180 configured to turn off the pump 180 when the pump 180 is no longer pulling fluid; and/or any other suitable means for preventing air from entering the fluid path.

FIG. 1 includes dimensions corresponding to the distance between various components of the system 100. These dimensions are only exemplary and other dimensions are possible depending on various manufacturing, operational, and/or therapeutic considerations including, for example, the size of the containers and/or other components included in the system 100 and/or the volume of reconstituted drug product to be produced.

Figure 2:
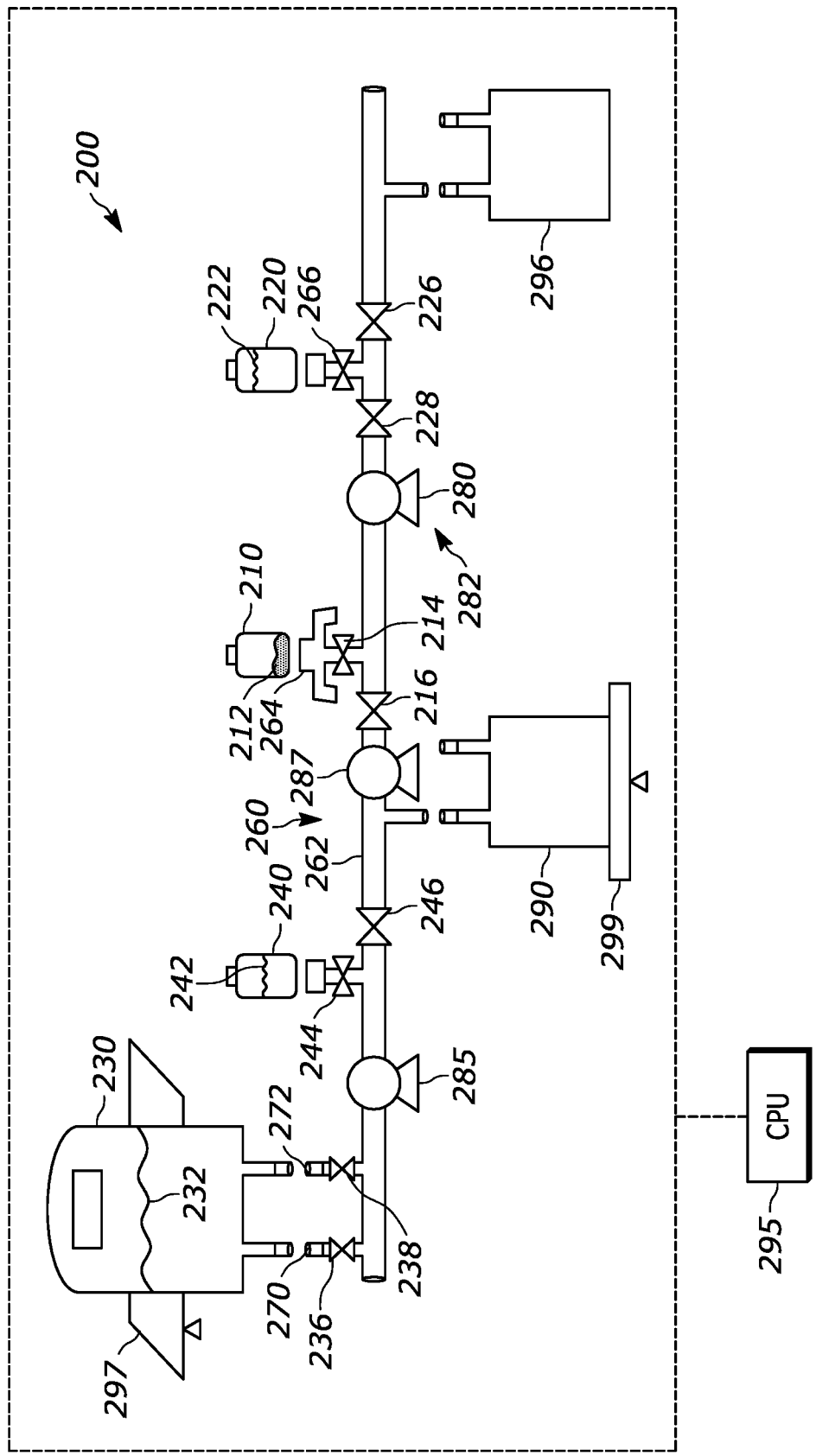
FIG. 2 illustrates exemplary drug reconstitution system in accordance with various embodiments.

The drug delivery system 200 shown in FIG. 2 includes, generally, a drug product container 210 containing a drug product 212; a diluent container 220 containing a diluent 222; a saline container 230 containing a saline solution 232; an IV stabilizing solution ("IVSS") container 240 containing an IVSS 242; and a fluid path assembly 260 configured to selectively, fluidly couple or de-couple various of the aforementioned components.

The system 200 shown in FIG. 2 includes many similar or identical components as those shown in FIG. 1 and described above. The elements of the system 200 not described in more detail here may have similar or identical configurations, functions, and/or structure as the correspondingly numbered elements described above with respect to the system 100 shown in FIG. 1.

One main difference from the system 100 in FIG. 1 is that the system 200 shown in FIG. 2 includes at least two pumps, 280, 285 that are each preferably relative fixedly connected with the fluid path assembly 260 rather than being easily removable therefrom as with the pump 180 in FIG. 1. Also, a third pump 287 may be utilized as well. The pumps 280, 285, 287 may include disposable pump heads (peristaltic or positive displacement). The pumps 280, 285, 287 may be driven by permanently mounted motor and shafts and are connected to a user interface and/or a pump controller (as discussed in more detail below).

The additional pump(s) 285, 287 allow the system 200 to be utilized or operated with fewer steps such as disconnecting and reconnecting a pump. As such, the system 200 may be suitable for use by individuals with less time to prepare a mixture and/or less training or experience in preparing relatively complex drug mixtures. For example, the system 200 may be suitable for use by a patient or a health care provider, in addition to a pharmacist. As a more specific example, the system 200 shown in FIG. 2 may enable patients to perform the reconstitution steps independently without the help of a pharmacist.

Figure 3:
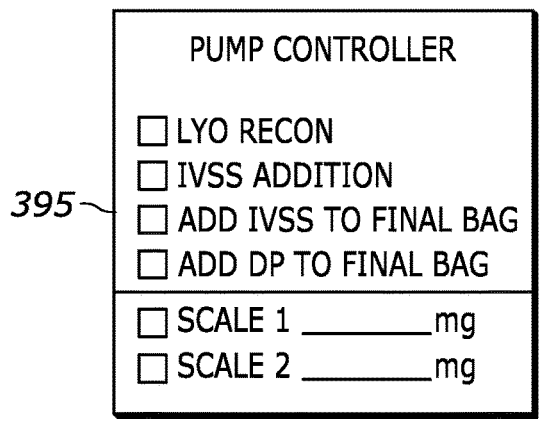
FIG. 3 illustrates exemplary controls components in accordance with various embodiments.

Another main difference is that the system 200 shown in FIG. 2 includes a controller 295 or a central processing unit ("CPU") for controlling all or some of the components of the system 200. For example, the system 200 may be able to be operated by the push of a button (or series of buttons) or other commands. As another example, the system 200 may be coupled with an external computer and/or a smart phone for controlling thereof. Such capabilities may require or utilize wireless communications components such as a Bluetooth or WiFi technology. As another example, FIG. 3 shows an exemplary controller and/or interface 395 that allows a user to control the operation of the system 200.

Another main difference is that the system 200 shown in FIG. 2 includes at least one scale, such as scale 297 weighing the saline container 230 and scale 299 weighing the final drug product container 290. The system 200 may utilize fewer or additional scales, as desired. The scales 297, 299 shown in FIG. 2 may permit a user to monitor the progress of the mixing steps. The scales 297, 299 shown in FIG. 2 may also or alternatively be coupled with the CPU 295 and/or the controller 395 so the CPU and/or controller 395 is able to use data from the scales 297, 299 for operation of the system 200. For example, input from the scales 297, 299 may be utilized by the CPU 295 and/or the controller 395 to determine the progress of a particular step and/or to determine when to move to a subsequent step in the process.

Additionally or alternatively, the scales 297 and/or 299 can be connected to the controller 395 to provide a real-time monitoring of the addition/reconstitution steps as a means to monitor the volume of the solution. In this concept, the patient can simply step through the steps on the user interface and the pumps/scales/valves will be controlled via electronic controller PCB module (not shown). For example, FIG. 3 shows a series of buttons that may be notification indicators (light-up, etc.) for notifying a user of the status of the mixing process and/or may be a series of input buttons (press-button, etc.) for the user to control the mixing process.

Figure 4:
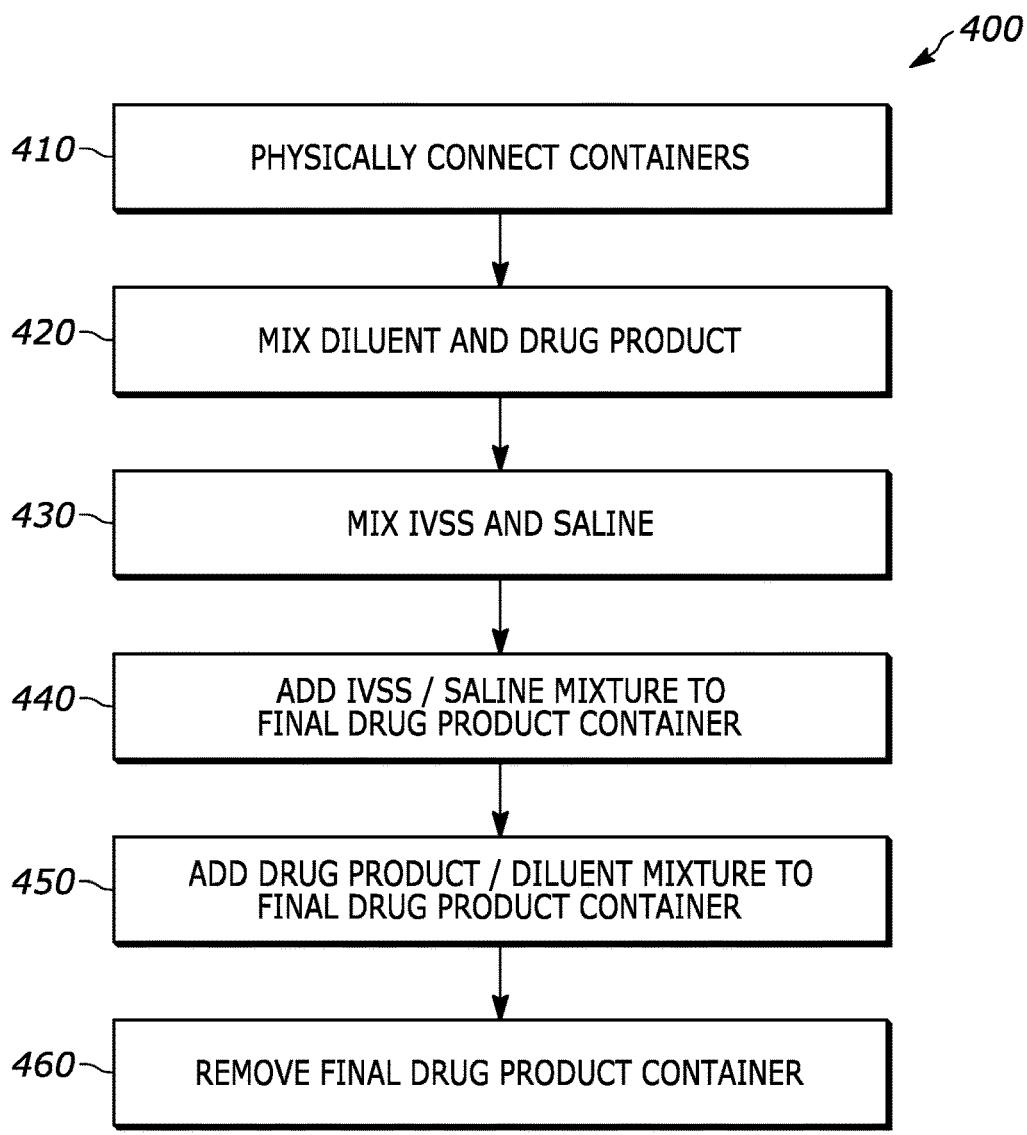
FIG. 4 illustrates an exemplary drug reconstitution method in accordance with various embodiments.

FIG. 4 shows an exemplary drug reconstitution method 400 in accordance with various embodiments. FIG. 4 includes the following steps:

step 410: physically connecting the containers (as described above, physical connection does not necessarily mean fluidly connecting) to the system;

step 420: mix diluent and drug product components, such as by utilizing the above-described or other appropriate steps;

step 430: mix the IVSS and saline components, such as by utilizing the above-described or other appropriate steps;

step 440: add the IVSS/saline mixture to the final drug product container, such as by utilizing the above-described or other appropriate steps;

step 450: add the drug product/diluent to the final drug product container, such as by utilizing the above-described or other appropriate steps; and step 460: remove the final drug product container for use and/or storage.

The above-described steps are exemplary and may be modified and/or performed in a different order than described above. Some or all of the above-described may be performed by or under the direction of a controller including, for example, the above-described controller 295 or controller 395. In some embodiments, the controller may be programmed to perform some or all of the above-described steps.

In some examples, the IVSS may be provided as a percentage of an overall volume of solution. In these examples, suitable quantities of IVSS may range between approximately 2% and approximately 15% (e.g., between approximately 1 mL in a 50 mL container and approximately 25 mL in a larger, 270 mL container). The IVSS can also act as a pretreating surfactant or a buffering component that prevents adsorption of the drug onto the walls of the container. For example, due to the highly potent nature of some drugs being administered, if the container is not sufficiently and properly coated with the IVSS, it may lead to an undesirable risk of drug molecules adhering or adsorbing to the inner walls of the container. In the event of adsorption of the drug onto the delivery container walls, the dosage of the drug may be adversely impacted. In such a situation, it may be desirable to utilize the exemplary steps discussed in the prior paragraph.

In some examples, the IVSS may include polysorbate. In some examples, the IVSS formulation may include approximately 1.25 M lysine monohydrocholoride, 25 mM citric acid monohydrate, 0.1% (w/v) polysorbate 80, and has a pH of approximately 7.0. In other examples, the IVSS 54 may include similar formulations, but also have a minimum of approximately 0.9% NaCl and approximately 0.001 to approximately 0.1% (w/v) polysorbate 80. It is appreciated that different BiTEs require different final percentages of IVSS 54 in the delivery container. This percentage may vary between approximately 0.5% to approximately 12% of the final volume in the delivery container. Further, citrate may increase the risk of glass delamination if filled in glass vials. In the event that citrate is necessary for drug product stabilization (determined on a per-product basis), the delivery containers may be constructed from CZ or other plastic compositions. Other examples of ingredients for suitable IVSSs are possible. Suitable IVSS concentrations protect against protein-plastic interactions and/or surface adsorption, and more specifically, in the lower end of the concentration range where even minor losses may potentially change the effective dose. The below table illustrates example component concentrations for varying IVSS concentrations:

may not require reconstitution. Nonetheless, the system includes an accurate quantity of drug product, and thus does not require the need to add additional quantities thereto in a sterile environment. In some examples, the API may be in the form of a half-life extended ("HLE") BiTE® and/or an IV-admin monoclonal antibody ("mAbs") as desired. These HLE BiTEs include an antibody Fc region that advantageously provides different drug properties such as longer and extended half-lives. Accordingly, such APIs may be preferred due to their ability to maintain protective levels in the patient for relatively longer periods of time. Nonetheless, in other examples, the API may be in the form of a canonical-BiTE that is to be administered in a professional healthcare environment.

In some embodiments, the drug delivery system may have an integrated reconstitution subsystem onboard to dilute a lyophilized drug into a liquid form. In certain such embodiments, a diluent reservoir may be included for storing a diluent solution and a lyophilized reservoir may be included storing a lyophilized compound separate from the diluent solution. Furthermore, a fluid drive mechanism may be

TABLE 1

Component Concentrations with Varying IVSS Concentrations (top column units are (V/N) % of IVSS

| | IVSS COMPONENTS | | | | | | | |
|---|---|---|---|---|---|---|---|---|
| | 0.5 | 1.0 | 2.0 | 4.0 | 6.0 | 8.0 | 10.0 | 12.0 |
| Lysine monohydrochloride (M) | 0.00625 | 0.0125 | 0.025 | 0.05 | 0.075 | 0.1 | 0.125 | 0.15 |
| Citrate Monohydrate (M) | 0.000125 | 0.00025 | 0.0005 | 0.001 | 0.0015 | 0.002 | 0.0025 | 0.003 |
| Polysorbate 80 (% w/N) | 0.0005 | 0.001 | 0.002 | 0.004 | 0.006 | 0.008 | 0.01 | 0.012 |

By providing the components in containers that are selectively connectable, it may be no longer necessary to prepare a needle and syringe assembly to inject one component into another container, to ensure that this prepared needle and syringe assembly is sterilized, and/or to ensure a correct volume or amounts of components are added together.

Some conventional systems may provide delivery containers having saline solution overfill, where more saline solution is provided in the delivery container than what is needed for dosage. In these systems, it may be necessary to remove a volume of the saline solution prior to preparing the drug dosage, which may require preparing a sterile withdrawal tool (e.g., a needle and syringe assembly) and carefully extracting an accurate amount of saline solution. Conversely, the disclosed systems may additionally eliminate this process, as the containers are prefilled with the required quantity of components. Additionally, the risk of a needle sticking due to the transfer of the components may also be reduced or mitigated.

Additionally, many or all of the above described steps may be automated or semi-automated or reduced in time/scope, thereby potentially saving time and effort for the persons preparing and/or using the drug.

As discussed above, the drug product container contains a predetermined quantity of drug product or active pharmaceutical ingredient ("API") (e.g., between approximately 2 mcg and approximately 100 mcg), depending on the BiTE® and container size, which, in the illustrated example, is in powdered form (i.e., lyophilized) requiring reconstitution. In other examples, the drug product may be in liquid form and included for mixing the diluent solution in the diluent reservoir with the lyophilized compound in the lyophilized reservoir. In some embodiments, the fluid drive mechanism may transfer the diluent solution from the diluent reservoir into the lyophilized reservoir and/or provide any circulation and/or agitation needed to achieve full reconstitution. In some embodiments, an additional final reconstituted drug reservoir may be included and serve as a delivery reservoir from which the reconstituted drug is discharged into the patient; whereas, in other embodiments, the lyophilized reservoir may serve as the delivery reservoir. While the reconstitution subsystem may be physically integrated into the drug delivery system in certain embodiments, in other embodiments the reconstitution subsystem may constitute a separate unit which is in fluid communication with the drug delivery system. Having a separate unit may simplify the reconstitution process for healthcare providers in certain cases.

The drug product container may be in the form of an IV bag, a vial, a prefilled syringe, or similar container that includes a reconstitution container body defining an inner volume. The inner volume may be sterile. In some approaches, the reconstitution container adapter may also be a CSTD (or, in examples where the prefilled reconstitution container is in the form of a syringe, the container adapter may be a needle) that mates, engages, and/or couples to the vial adapter. Additionally or alternatively, the drug product can be bulk lyophilized and filled into a cartridge or container that is typically used to administer with an IV pump. If needed the dehydrated forms of IVSS, NaCl, and any other components needed for the final administered solution can be bulk lyo'ed and filled into the cassette for long term storage.

The prefilled diluent container contains a predetermined quantity of diluent (e.g., preservative-free water for injection or "WFI") (e.g., between approximately 0.5 mL and approximately 10 mL) to be added to the prefilled drug product container for reconstitution of the drug product. In some examples, a benzyl alcohol preserved (or any other preservative) WFI may be used.

As previously noted, in some examples, the prefilled drug product container may be in the form of a prefilled syringe that contains the drug product. In these examples the drug product may be in the form of a liquid BiTE® formulation used in conjunction with a monoclonal antibody (mAb), In these examples, the drug product may be directly added to the delivery container without the use of a vial adapter system (such as the above-mentioned CSTDs) where more traditional needle-syringe injection/delivery into the container is preferred, which may advantageously simplify and/or improve supply chain and manufacturing control, and may further allow for more compact commercial packaging that takes up less space in storage systems at healthcare facilities. In these examples, the prefilled drug product vial may or may not need to be reconstituted prior to transferring the drug product to the delivery container.

The system may be distributed and/or sold as a common kit packaging, but other suitable distribution/packaging is suitable. The drug product may be in the form of a half-life extended bispecific T cell engager (BiTE®), but other drug products are suitable. The diluent include water for injection ("WFI"), but other diluents may be suitable. The containers may be pliable bags, such as IV bags, but other containers may be suitable. In some examples, one or more of the containers is in the form of an IV drip bag constructed from a plastic or other material, e.g., 250 mL 0.9% Sodium Chloride IV bag constructed of a suitable material such as polyolefin, non-DEHP (diethylhexl phthalate), PVC, polyurethane, or EVA (ethylene vinyl acetate) and can be filled to a volume of approximately 270 mL to account for potential moisture loss over long-term storage.

During some or all of the above steps, the contents of a container may then be gently stirred, swirled, and/or inverted to mix the ingredients, thereby forming a desired mixture. Similarly, the mixtures may be visually inspected for imperfections and/or to ensure adequate mixing has occurred.

The system may be used to provide intravenous, subcutaneous, intra-arterial, intramuscular, and/or epidural delivery approaches. By using the system, patient anxiety and or confusion may be reduced due to reduced preparation complexity and wait times caused by the drug preparation process.

In some examples, the prefilled delivery container is in the form of an IV drip bag constructed from a plastic or other material, e.g., 250 mL 0.9% Sodium Chloride IV bag constructed of a suitable material such as polyolefin, non-DEHP (diethylhexl phthalate), PVC, polyurethane, or EVA (ethylene vinyl acetate) and can be filled to a volume of approximately 270 mL to account for potential moisture loss over long-term storage. Other examples of suitable delivery containers are possible such as, for example, a glass bottle or container. Example suitable prefilled delivery containers are described in U.S. Appln. No. 62/804,447, filed on Feb. 12, 2019 and U.S. Appln. No. 62/877,286 filed on Jul. 22, 2019, the contents of each of which are incorporated by reference in their entirety.

At least one of the delivery container adapters may be a closed system transfer device ("CSTD") that allows for transfer of the drug and/or fluids into the container body. Example CSTD devices may include the OnGuard CSTD provided by B. Braun Medical Inc, BD PhaSeal CSTD components, Equashield CSTD, Codon CSTD, and the like. Further, non-closed system transfer devices may be used such as West Pharmaceuticals vial and bag adapters. Other examples are possible. The prefilled delivery container may include any number of delivery container adapters having different specifications (e.g., port sizes) to accommodate the use of different drug product vials.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Epo-ratio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RAN KL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry No. 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti- CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to half-life extended BiTEs that include an antibody Fc region, BLIN-CYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug reconstitution system comprising:
   a first component selected from a group of a drug product, a diluent, a saline solution, and an IV stabilizing solution ("IVSS"), wherein the first component is in a first container in a storage state;
   a second component selected from a group of the drug product, the diluent, the saline solution, and the IVSS, wherein the first component is different than the second component and the second component is in a second container in a storage state;
   a third component selected from a group of the drug product, the diluent, the saline solution, and the IVSS, wherein the third component is different than the first component and the second component, wherein the third component is in a third container in a storage state;
   a fourth component selected from a group of the drug product, the diluent, the saline solution, and the IVSS, wherein the fourth component is different than the first component, the second component, and the third component, wherein the fourth component is in a fourth container in a storage state;
   at least one fluid path configured to at least selectively fluidly connect the first container and the second container;
   an urging assembly configured to selectively urge at least a portion of the first component from the first container and into contact with the second component to mix the first component and the second component within a first portion of the at least one fluid path; and
   at least one valve configured to selectively fluidly isolate the first portion of the at least one fluid path and a second portion of the at least one fluid path fluidly coupled with the third container and the fourth container.

2. The drug reconstitution system as in claim 1, wherein the urging assembly includes at least one of the following: a pump at least selectively coupled with the at least one fluid path, at least one fluid path valve, at least one fluid path clamp, at least one fluid path closing component, at least one gravitational flow differential, a ramped surface, or a raised container support.

3. The drug reconstitution system as in claim 1, wherein the first container, the second container, and third container are from a common kit packaging.

4. The drug reconstitution system as in claim 3, wherein the first container, the second container, and the third container are packaged in the common kit packaging such that a sterile connection exists between the at least one fluid path and each of the first container, the second container, and the third container.

5. The drug reconstitution system as in claim 1, wherein the first container, the second container, and the third container connect to the at least one fluid path at distinct locations such that the first container, the second container, and the third container are connected in series by the at least one fluid path.

6. The drug reconstitution system as in claim 1, wherein the first container, the second container, third container, and the fourth container are from a common kit packaging.

7. The drug reconstitution system as in claim 6, wherein the first container, the second container, the third container, and the fourth container are packaged in the common kit packaging such that a sterile connection exists between the at least one fluid path and each of the first container, the second container, the third container, and the fourth container.

8. The drug reconstitution system as in claim 1, wherein the first container, the second container, the third container, and the fourth container connect to the at least one fluid path at distinct locations such that the first container, the second container, the third container, and the fourth container are connected in series by the at least one fluid path.

9. The drug reconstitution system as claim 1, wherein the drug product is in the form of a bispecific T cell engager.

10. The drug reconstitution system as in claim 9, wherein the bispecific T cell engager is a half-life extended (HLE) bispecific T cell engager.

11. A method of preparing a drug for delivery, the method comprising:
  providing a diluent contained in a diluent container;
  providing a drug product contained within a drug product container;
  providing a saline solution contained in a saline container;
  providing an IV stabilizing solution ("IVSS") contained in an IVSS container;
  providing a fluid path system physically connecting the diluent container, the drug product container, the saline container, and the IVSS container, the fluid path system having:
    a storage configuration wherein the fluid path system is coupled with each of the diluent container, the drug product container, the saline container, and the IVSS container, the diluent container and the drug product container are not in fluid communication with each other, and the saline container and the IVSS container are not in fluid communication with each other,
    a first mixing configuration wherein the diluent container and the drug product container are in fluid communication with each other via a first portion of the fluid path system, and
    a second mixing configuration wherein the saline container and the IVSS container are in fluid communication with each other via a second portion of the fluid path system; and
  adjusting the fluid path system from the storage configuration to the first mixing configuration to urge at least a portion of the diluent from the diluent container and/or at least a portion of the drug product from the drug product container to form a drug product/diluent mixture.

12. The method of claim 11, wherein the step of adjusting the fluid path system from the storage configuration to the first mixing configuration includes opening a valve.

13. The method of claim 11, wherein the step of adjusting the fluid path system from the storage configuration to the first mixing configuration includes removing a clamp.

14. The method of claim 11, further comprising the steps of:
  adjusting the fluid path system to the second mixing configuration to urge at least a portion of the saline solution from the saline container and/or at least a portion of the IVSS from the IVSS container to form a saline/IVSS mixture.

15. The method of claim 14, further comprising the steps of:
  adjusting the fluid path system from the storage configuration to a third mixing configuration to urge at least a portion of the drug product/diluent mixture and at least a portion of the saline/IVSS mixture into fluid communication with each other.

16. The method of claim 15, further comprising the steps of:
  providing a pump to be selectively coupled with the fluid path system; and
  adjusting the position of the pump between a first position and a second position during at least two of the first, second, and third mixing configuration steps.

* * * * *